(12) United States Patent
Legagneux et al.

(10) Patent No.: US 12,384,974 B2
(45) Date of Patent: Aug. 12, 2025

(54) METHOD FOR CAPTURING SILICON AT LOW HOURLY SPACE VELOCITY

(71) Applicant: IFP ENERGIES NOUVELLES, Rueil Malmaison (FR)

(72) Inventors: Nicolas Legagneux, Rueil Malmaison (FR); Marie-Claire Marion, Rueil Malmaison (FR); Karin Barthelet, Rueil Malmaison (FR)

(73) Assignee: IFP ENERGIES NOUVELLES, Rueil Malmaison (FR)

( * ) Notice: Subject to any disclaimer, the term of this patent is extended or adjusted under 35 U.S.C. 154(b) by 149 days.

(21) Appl. No.: 18/268,174

(22) PCT Filed: Dec. 9, 2021

(86) PCT No.: PCT/EP2021/084890
§ 371 (c)(1),
(2) Date: Jun. 16, 2023

(87) PCT Pub. No.: WO2022/135944
PCT Pub. Date: Jun. 30, 2022

(65) Prior Publication Data
US 2024/0059981 A1 Feb. 22, 2024

(30) Foreign Application Priority Data
Dec. 21, 2020 (FR) ........................ 2013848

(51) Int. Cl.
*B01D 53/46* (2006.01)
*B01D 53/44* (2006.01)
*B01D 53/82* (2006.01)
*B01J 20/02* (2006.01)
*B01J 20/08* (2006.01)
*B01J 20/28* (2006.01)
*C07C 7/163* (2006.01)
*C10G 25/00* (2006.01)
*C10G 29/04* (2006.01)
*C10G 67/02* (2006.01)
*C10G 67/06* (2006.01)
*C10L 3/10* (2006.01)

(52) U.S. Cl.
CPC ........... *C10G 25/003* (2013.01); *B01D 53/46* (2013.01); *B01D 53/82* (2013.01); *B01J 20/08* (2013.01); *B01J 20/28011* (2013.01); *B01J 20/28061* (2013.01); *B01J 20/28071* (2013.01); *B01J 20/28073* (2013.01); *B01J 20/28076* (2013.01); *B01J 20/28083* (2013.01); *C10L 3/101* (2013.01); *B01D 2253/1124* (2013.01); *B01D 2253/25* (2013.01); *B01D 2253/306* (2013.01); *B01D 2253/308* (2013.01); *B01D 2253/311* (2013.01); *B01D 2257/55* (2013.01); *B01J 2220/56* (2013.01); *C10G 2300/1003* (2013.01); *C10G 2300/1022* (2013.01); *C10G 2300/1025* (2013.01); *C10G 2300/104* (2013.01); *C10G 2300/202* (2013.01)

(58) Field of Classification Search
CPC .......... B01D 2251/61; B01D 2253/104; B01D 2253/1124; B01D 2253/25; B01D 2253/306; B01D 2253/308; B01D 2253/311; B01D 2257/55; B01D 2257/553; B01D 2257/556; B01D 2258/0283; B01D 2258/05; B01D 53/44; B01D 53/46; B01D 53/82; B01J 20/02; B01J 20/08; B01J 20/28011; B01J 20/28057; B01J 20/28061; B01J 20/28069; B01J 20/28071; B01J 20/28073; B01J 20/28076; B01J 20/2808; B01J 20/28083; B01J 2220/56; C07C 7/1485; C07C 7/163; C07C 9/04; C10G 2300/1003; C10G 2300/1022; C10G 2300/1025; C10G 2300/104; C10G 2300/202; C10G 25/003; C10G 29/04; C10G 67/02; C10G 67/06; C10L 2290/542; C10L 3/101
See application file for complete search history.

(56) References Cited

U.S. PATENT DOCUMENTS

| | | | |
|---|---|---|---|
| 4,645,587 A | 2/1987 | Kokayeff | |
| 2003/0092570 A1 | 5/2003 | Teshigawara et al. | |
| 2012/0107201 A1 | 5/2012 | Kim et al. | |
| 2016/0046881 A1* | 2/2016 | Shih | C10G 67/06 208/97 |

(Continued)

FOREIGN PATENT DOCUMENTS

| | | | |
|---|---|---|---|
| CN | 1478862 A | * | 3/2004 |
| CN | 101683623 B | | 1/2012 |
| CN | 101457158 B | * | 4/2013 |

(Continued)

OTHER PUBLICATIONS

CN1478862A Translation BIB (Year: 2004).*

(Continued)

*Primary Examiner* — Ellen M McAvoy
*Assistant Examiner* — Chantel Graham
(74) *Attorney, Agent, or Firm* — Millen, White, Zelano & Branigan, P.C.; Csaba Henter

(57) ABSTRACT

The present invention relates to a process for trapping silicon compounds in a gaseous or liquid feedstock, comprising bringing the feedstock into contact with a trapping mass with a liquid hourly space velocity LHSV of less than 5 $h^{-1}$ or a gas hourly space velocity GHSV of less than 500 $h^{-1}$.

20 Claims, No Drawings

(56) References Cited

U.S. PATENT DOCUMENTS

2019/0126201 A1 5/2019 Jakobsson et al.
2019/0201842 A1 7/2019 Jakobsson et al.

FOREIGN PATENT DOCUMENTS

| EP | 1317952 A1 | 6/2003 |
|----|------------|--------|
| JP | 2003286496 A | 10/2003 |
| WO | 2017202582 A1 | 11/2017 |
| WO | 2018073041 A1 | 4/2018 |
| WO | 2018189027 A1 | 10/2018 |

OTHER PUBLICATIONS

CN1478862A Translation Claims (Year: 2004).*
CN1478862A Translation Description (Year: 2004).*
CN101457158B Translation (Year: 2016).*
International Search Report for PCT/EP2021/084890 dated Jun. 2, 2022.
English Abstract of JP2003286496, Publication Date: Oct. 10, 2003.
English Abstract of WO2018189027, Publication Date: Oct. 18, 2018.
English Abstract of CN101457158, Publication Date: Jun. 17, 2009.
English Abstract of CN101683623, Publication Date: Mar. 31, 2010.

* cited by examiner

METHOD FOR CAPTURING SILICON AT LOW HOURLY SPACE VELOCITY

TECHNICAL FIELD

The present invention relates to a process for purifying hydrocarbon feedstocks via a step of removing silicon by contact with a solid.

PRIOR ART

Certain hydrocarbon feedstocks are likely to contain impurities which can be poisons for the catalysts which have to be employed to refine them. Sulfur and nitrogen are impurities very often present in feedstocks resulting from oil refining but also those resulting, for example, from the combustion of solid feedstocks, such as, for example, biomass or else a mixture of plastics. These feedstocks can also contain silicon, which is a poison for many catalysts, such as, for example, hydrogenation, hydrotreating and catalytic reforming catalysts.

For example, one of the sources of contamination of hydrocarbon feedstocks by silicon is the addition of defoamers to the feedstocks before their treatment. This is because certain processes employed in petroleum processes (stirring, distillation, combustion, cracking) used during the refining of crude oil can result in the formation of emulsions. This is the case, for example, during the generation of vapors and in the presence of natural surfactants (asphaltenes and resins). However, the presence of foams can cause many operating and maintenance problems and detrimentally affect the efficiency. Defoamers are often based on silicon, more generally called silicones, because of their surface properties and their relative thermal stability, the most widely used in the petroleum industry being polydimethylsiloxane or PDMS. Despite a high thermal stability, the high temperature ($\geq 300°$ C.) within the refining processes nevertheless leads to a degradation of the polymer to give a mixture of lighter organosilicon compounds. In the case of PDMS, the predominant degradation compounds are cyclic siloxanes (see, for example, G. Camino, S. M. Lomakin and M. Lazzari, "Polydimethylsiloxane Thermal Degradation Part 1. Kinetic Aspects", Polymer, 2001, 42(6), pp. 2395-2402). Other types of compounds can be formed, such as, for example, silanols and linear siloxanes.

In addition, the places where a defoamer is likely to be added are during extraction of the oil, before the hydrocarbon feedstock enters the distillation column, in the thermal cracking (coking, visbreaking and steam cracking) or propane desalphalting units.

The amounts of silicon found in the various effluents downstream of these units depend on their number and the cut points chosen. For example, a silicon content which can reach 50 ppm by weight is measured in gasoline cuts resulting from coking units (coker naphtha), on average from 10 to 15 ppm by weight.

The silicon can exist in two distinct forms:
the silicon referred to as mineral silicon, which may result for example from debris from refractory beads or plastic additives. It is present physically but does not seem to be bound to disturb the activity or the selectivity of the catalyst concerned; and
the silicon usually referred to as organic. The silicon is then included in organosilicon compounds. Said silicon can react with the surface groups of the catalysts, in particular with surface hydroxyls (see, for example, L. Kellberg, P. Zeuthe and H. J. Jakobsen, "Deactivation of HDT catalysts by formation of silica gels from silicone oil, characterization of spent catalysts from HDT of coker naphtha using Si and C CP-MAS NMR", Journal of Catalysis, 1993, 143(1), pp. 45-51), which results in an irreversible poisoning of the catalysts.

Inter alia, to avoid the poisoning of the catalysts, it is desired to remove or at least reduce the concentration of silicon, in particular in organic form, in the hydrocarbon feedstocks to be refined.

Industrially, to protect catalysts at risk of being poisoned by silicon, a dedicated trapping mass is positioned upstream of said catalysts. The silicon-contaminated feedstock will thus be brought into contact beforehand with this mass before being brought into contact with the catalysts to be protected. Said contact with the trapping mass can be carried out in a first bed placed before the bed or beds of catalysts to be protected. Said contact can also be carried out in an independent dedicated chamber as described, for example, in patent EP 1 925 654. The effluent resulting from this stage of trapping of the organosilicon compounds is then purified.

Several patents propose alumina-based trapping masses. For example, U.S. Pat. No. 4,176,047 suggests the use of alumina, activated alumina or a spent catalyst. U.S. Pat. No. 4,645,587 describes the use of a mass based on a copper compound supported on alumina. Other documents, such as U.S. Pat. Nos. 7,713,408, 5,118,406 or else patent application US 2018/237706 recommend the use of a mass of hydrotreating catalyst type, namely an alumina containing at least one group VIII metal and at least one group VIB metal, or even a phosphorus compound.

In order for the processes for purifying, by silicon removal, a hydrocarbon feedstock contaminated by silicon-containing species to be more effective, one of the options is to improve the trapping capacity of the trapping masses used, for example by modifying the nature of the trapping mass and/or by modifying the operating conditions. For example, it is generally accepted that temperature has a beneficial effect, as illustrated in the article "Novel Coker Naphtha Hydrotreating Technology" by R. Breivik and R. Egebjerg from Haldor Topsoe, ERTC 12th Annual Meeting (2007).

U.S. Pat. Nos. 6,576,121 and 8,106,250 claim greater trapping of silicon species by the prior addition of water to the feedstock, in a proportion of between 0.01% and 10% by volume, preferably between 0.1% and 3% by volume. Indeed, they claim that this addition of water makes it possible to maximize the number of surface hydroxyls and therefore the trapping of silicon compounds.

However, the liquid/gas hourly space velocity (LHSV/GHSV) is not expected to have an impact on the saturation trapping capacity of the trapping masses. Here, LHSV and GHSV are defined as the volume of (liquid or gaseous) feedstock divided by reactor volume per hour. Specifically, modifying the liquid or gas hourly space velocity leads to a modification of the contact time which can affect the shape of the breakthrough curve but, for those skilled in the art, not the trapping capacity. Some have also reported that the liquid or gas hourly space velocity had no impact on the performance of the masses in trapping silicon (see the article by M. Notermann, "A comparative study of silicone adsorption on hydrotreating catalysts", AICHE Spring Nat. Meet. 1993. Others mention that it is preferable to operate at high LHSV (see patent application US 2018/0237706), and more specifically recommend an LHSV$\geq 5$ h$^{-1}$.

Thus, according to the prior art, the purification processes for removing silicon from a hydrocarbon feedstock contaminated by silicon-containing species are processes in which the removal of the silicon is carried out by contact of the contaminated feedstock with a solid of adsorbent type, which contact is preferentially carried out at high liquid or gas hourly space velocity.

SUMMARY OF THE INVENTION

In the context described above, a first object of the present description is to overcome the problems of the prior art and to provide an improved process for trapping silicon compounds and in particular organosilicon compounds.

Surprisingly, the applicant has identified that the removal of the organosilicon species could be advantageously improved by reducing the liquid or gas hourly space velocity and more particularly by operating at an LHSV<5 h$^{-1}$ or at a GHSV<500 h$^{-1}$.

The trapping process according to the invention is improved compared to the prior art because said process makes it possible to significantly improve the effectiveness of the mass in trapping silicon, an impurity of the feedstock, while simplifying and minimizing the operations and the production costs. Effectiveness of the mass is understood to mean significantly increased performance qualities in trapping capacity (more than 50% capacity). The gain in performance quality (the increase in the capacity of the mass) translates into significant advantages. The gain in performance quality makes it possible to increase the cycle time of the mass and simplifies the process and thus reduces the operating costs. The gain in performance quality also makes it possible to better protect the catalysts of the downstream processes (in particular those of the hydrodesulfurization, hydrotreating or reforming processes) and also results in their lifetime being improved, which simplifies the process and further reduces the operating costs.

According to a first aspect, the aforementioned objectives, and other advantages, are obtained by a process for trapping silicon compounds in a gaseous or liquid feedstock, comprising bringing the feedstock into contact with a trapping mass with a liquid hourly space velocity LHSV of less than 5 h$^{-1}$ or a gas hourly space velocity GHSV of less than 500 h$^{-1}$. The LHSV is the volume of liquid feedstock divided by the reactor volume and per hour. The GHSV is the volume of gas feedstock divided by the reactor volume and per hour.

According to one or more embodiments, the LHSV is less than 4.5 h$^{-1}$, preferably less than 4.25 h$^{-1}$. According to one or more embodiments, the GHSV is less than 450 h$^{-1}$, preferably less than 425 h$^{-1}$.

According to one or more embodiments, the contact is carried out at a temperature of between 20° C. and 500° C., preferably between 100° C. and 450° C., preferably between 150° C. and 430° C., and a pressure of between 0.1 and 10 MPa.

According to one or more embodiments, the contact is carried out in the presence of dihydrogen, wherein the feedstock is liquid and the ratio of the gaseous volume flow rate of dihydrogen to the liquid volume flow rate of liquid feedstock is between 0 and 1000 Nm$^3$/m$^3$, preferably between 0.1 and 750 Nm$^3$/m$^3$, preferably between 1 and 500 Nm$^3$/m$^3$, or wherein the feedstock is gaseous and the dihydrogen partial pressure PpH$_2$ is between 0.01 MPa (0.1 bar) and 10 MPa or 9 MPa (100 bar or 90 bar), preferably between 0.1 MPa (1 bar) and 5 MPa (50 bar).

According to one or more embodiments, the trapping mass is arranged in a fixed bed.

According to one or more embodiments, the process uses a plurality of trapping masses positioned in a mixture or multilayer.

According to one or more embodiments, the process uses trapping masses arranged in a trapping unit comprising at least two reactors, positioned in series or in parallel. According to one or more embodiments, said reactors are equipped with a bypass line making it possible at the same time to bypass a first reactor, the trapping mass of which is saturated, and to treat the feedstock in the second reactor without shutting down the unit.

According to one or more embodiments, the operating conditions of each of the reactors are identical or different.

According to one or more embodiments, the process further comprises a pretreatment step upstream of the contacting step in order to reduce or eliminate unsaturated organic compounds, preferably coke precursor compounds, preferably diolefins, or any other undesirable impurity, preferably compounds comprising sulfur, nitrogen, and/or a metal.

According to one or more embodiments, the pretreatment step is a selective hydrogenation step.

According to one or more embodiments, the effluent depleted in silicon compounds is sent to a hydrotreating section, preferably to reduce the sulfur content and/or nitrogen content.

According to one or more embodiments, the trapping mass is positioned at the inlet of a hydrotreating reactor.

According to one or more embodiments, the trapping mass contains alumina and optionally at least one metal chosen from the metals from group VIB and group VIII. According to one or more embodiments, the trapping mass contains phosphorus.

According to one or more embodiments, the trapping mass has at least one of the following characteristics: γ-type support, presence of group VIB metal with a content of less than 20% by weight of group VIB metal expressed as oxide, presence of group VIII metal with a content of less than 10% by weight of group VIII metal expressed as oxide, presence of phosphorus with a content of less than 15% by weight of P expressed as oxide P$_2$O$_5$, grain density at least 0.2 g/ml, specific surface area at least 200 m$^2$/g, average pore size of less than 50 nm, total pore volume of between 0.15 cm$^3$/g and 1.5 cm$^3$/g.

According to one or more embodiments, the feedstock is chosen from the group consisting of combustion flue gases, synthesis gas, natural gas, natural-gas condensates, petroleum or petroleum crudes, liquid or gaseous petroleum cuts, liquid hydrocarbon cuts from refineries or petrochemical plants, effluents resulting from Fischer-Tropsch synthesis processes, petrochemical intermediates, oils resulting from the pyrolysis of biomass or plastics, biogas, coking gasoline or catalytic cracking gasoline, and mixtures thereof.

Embodiments according to the abovementioned aspects and also other characteristics and advantages will become apparent on reading the description which will follow, given solely by way of illustration and without limitation.

DESCRIPTION OF THE EMBODIMENTS

Embodiments of the invention will now be described in detail. In the following detailed description, many specific details are presented in order to provide a deeper understanding of the invention. However, it will be apparent to a person skilled in the art that the invention can be implemented without these specific details. In other cases, well-known characteristics have not been described in detail in order to avoid unnecessarily complicating the description.

Definitions

The textural and structural properties of the trapping mass are determined by the characterization methods known to a person skilled in the art.

In the account which follows of the invention, specific surface area is understood to mean the BET specific surface area determined by nitrogen adsorption in accordance with the standard ASTM D 3663-78 drawn up from the Brunauer-Emmett-Teller method described in the journal "The Journal of the American Chemical Society", 60, 309 (1938).

The pore volume, the grain density, the mean size (or mean diameter) of the pores and the pore distribution are determined by mercury porosimetry (see Rouquerol F.; Rouquerol J.; Singh K. "Adsorption by Powders & Porous Solids: Principle, Methodology and Applications", Academic Press, 1999). More particularly, the pore volume is measured by mercury porosimetry according to the standard ASTM D4284-92 with a wetting angle of 140°, for example by means of an Autopore III™ model device from the brand Micromeritics™.

In the mercury porosimetry technique, Kelvin's law is applied, which law gives the relationship between the pressure, the diameter of the smallest pore into which the mercury penetrates at said pressure, the wetting angle and the surface tension according to the following formula in which Ø represents the diameter of the pore (nm), t the surface tension (48.5 Pa), θ the contact angle (θ=140 degrees) and P the pressure (MPa): $Ø=(4t \cos θ).10/P$ In the text hereinbelow, the groups of chemical elements are given according to the CAS classification (CRC Handbook of Chemistry and Physics, published by CRC Press, editor-in-chief D. R. Lide, 81st edition, 2000-2001). For example, group VIII according to the CAS classification corresponds to the metals from columns 8, 9 and 10 according to the new IUPAC classification; group VIB according to the CAS classification corresponds to the metals from column 6 according to the new IUPAC classification.

In the present application, the term "to comprise" is synonymous with (means the same thing as) "to include" and "to contain", and is inclusive or open and does not exclude other elements not stated. It is understood that the term "to comprise" includes the exclusive and closed term "to consist". The term "based on" is synonymous with "comprises at least 50% by weight of". By default, the percentages given are % by weight. In addition, in the present description, the terms "essentially" or "substantially" correspond to an approximation of ±5%, preferably of ±1%, very preferably of ±0.5%. For example, an effluent comprising essentially or consisting of compounds A corresponds to an effluent comprising at least 95% by weight of compounds A.

The contents of metals from group VIII and from group VIB and of phosphorus are measured by X-ray fluorescence. The contents of metal from group VIB, of metal from group VIII and of phosphorus in the trapping mass are expressed as oxides after correction for the loss on ignition of the catalyst sample at 550° C. in a muffle furnace for two hours. The loss on ignition is due to the loss of moisture. It is determined according to ASTM D7348.

EMBODIMENTS

The present invention relates to a process for purifying hydrocarbon feedstocks via a step of removing silicon by contact with a trapping mass. It relates in particular to an improved process for purification by trapping silicon wherein the trapping capacity is increased by decreasing the liquid or gas hourly space velocity.

The process according to the invention is a process wherein a hydrocarbon feedstock, contaminated by contaminants which comprise at least species which contain the element Si, is purified by contact with a trapping mass, at a liquid hourly space velocity LHSV of less than 5 h$^{-1}$ or a gas hourly space velocity GHSV of less than 500 h$^{-1}$.

In the present application, the term "LHSV" signifies the liquid hourly space velocity of the sulfidation feedstock (liquid mixture) with respect to the volume of the trapping mass, that is to say the volume of the liquid feedstock divided by the reactor volume and per hour. "GHSV" is understood to mean the gas hourly space velocity of the sulfidation feedstock (gas mixture) with respect to the volume of the trapping mass, that is to say the volume of the gaseous feedstock divided by the reactor volume and per hour. The reactor volume comprises the volume of the trapping mass and the "empty" volume between the grains.

According to one or more embodiments, the LHSV is less than or equal to 4.5 h$^{-1}$ and preferably the LHSV is less than or equal to 4.25 h$^{-1}$. According to one or more embodiments, the LHSV is less than or equal to 4 h$^{-1}$, preferably less than or equal to 3 h$^{-1}$ and preferably less than or equal to 2 h$^{-1}$. According to one or more embodiments, the LHSV is of between 0.1 and 4.9 h$^{-1}$, preferably between 0.15 and 4.5 h$^{-1}$, preferably between 0.2 and 4.25 h$^{-1}$ and more preferably still between 0.25 and 4 h$^{-1}$.

According to one or more embodiments, the GHSV is less than or equal to 450 h$^{-1}$ and preferably the GHSV is less than or equal to 425 h$^{-1}$. According to one or more embodiments, the GHSV is less than or equal to 400 h$^{-1}$, preferably less than or equal to 300 h$^{-1}$ and preferably less than or equal to 200 h$^{-1}$. According to one or more embodiments, the GHSV is of between 10 and 490 h$^{-1}$, preferably between 150 and 450 h$^{-1}$, preferably between 20 and 425 h$^{-1}$ and more preferably still between 25 and 400 h$^{-1}$.

Specifically, the applicant has identified that, below 5 h$^{-1}$ for a liquid feedstock and 500 h$^{-1}$ for a gaseous feedstock, reducing LHSV by one unit or GHSV by around a hundred units made it possible to gain from 5% to 50% trapping capacity whereas, above these values, it only makes it possible to gain less than 5% trapping capacity. Surprisingly, there is a threshold value for LHSV and GHSV above which the hourly space velocity has only a slight impact. This means that, below a certain contact time (the contact time being inversely proportional to the hourly space velocity), the contact time has little impact on the trapping capacity of the trapping mass. Conversely, beyond a threshold value, increasing the contact time makes it possible to trap more silicon.

This contacting of the effluent to be treated with the trapping mass in the process according to the invention can be carried out at a temperature between 20° C. and 500° C., preferentially between 100° C. and 450° C., and more preferentially between 150° C. and 430° C., such as between 230 and 400° C. In addition, the contact of the feedstock to be treated with the trapping mass can be carried out at an absolute pressure of between 0.1 MPa (1 bar) and 20 MPa (200 bar), preferentially between 0.5 MPa (5 bar) and 10 MPa (100 bar), very preferentially between 1 MPa (10 bar) and 6 MPa (60 bar) or between 1 MPa (10 bar) and 5 MPa (50 bar), and very preferentially between 1 MPa (20 bar) and 4 MPa (50 bar).

During the step of bringing the feedstock to be treated into contact with the trapping mass, dihydrogen in gaseous form can be added to the feedstock. For example, the ratio by volume of the dihydrogen to the liquid feedstock to be treated can be between 0 and 1000 $Nm^3/m^3$, preferably between 0.1 and 750 $Nm^3/m^3$ and more preferably still between 1 and 500 $Nm^3/m^3$, or between 10 and 400 $Nm^3/m^3$, such as between 100 and 200 $Nm^3/m^3$ (e.g. 100±10 $Nm^3/m^3$). In the case of a gaseous feedstock, dihydrogen can be added so as to obtain a $PpH_2$ of between 0.01 MPa (0.1 bar) and 10 or 9 MPa (100 or 90 bar), preferably between 0.1 MPa (1 bar) and 5 MPa (50 bar).

Surprisingly, the applicant company has also identified that the removal of organosilicon species could be advantageously carried out in the absence of hydrogen (for example for the treatment of combustion flue gases). Thus, the trapping process according to the invention makes it possible to effectively trap silicon, an impurity of the feedstock, while improving atom economy, simplifying the process, reducing the equipment necessary for the operation of the process, and reducing the energy costs, the production costs and the operating costs. According to one or more embodiments, the step of removing silicon by contact with a trapping mass is carried out in the absence of hydrogen. According to this or these embodiment(s), the term "in the absence of hydrogen" is synonymous with: in the case of a liquid feedstock to be treated, a volume ratio between the dihydrogen and the feedstock of less than 0.1 $Nm^3/m^3$, preferably less than 0.01 $Nm^3/m^3$, preferably less than 0.001 $Nm^3/m^3$ and more preferably still less than 0.0001 $Nm^3/m^3$; and, in the case of a gaseous feedstock to be treated, a partial pressure of dihydrogen $PpH_2$ of less than 0.01 MPa, preferably less than 1 kPa, preferably less than 0.1 kPa and more preferably still less than 0.01 kPa.

The process according to the invention can be carried out according to any method known to those skilled in the art. Preferably, the process according to the invention is a fixed-bed process.

According to one or more embodiments, several trapping masses are used. The trapping masses can be in a mixture or in multilayers. According to one or more embodiments, the trapping mass or masses are used in one or more reactors, installed in series or in parallel. According to one or more embodiments, trapping masses are used in several reactors, the operating conditions of said reactors being identical or different.

According to one or more embodiments, the masses for trapping silicon species are used in at least two reactors, and the process according to the invention is advantageously carried out without the trapping of the silicon species being stopped, for example according to a lead-lag process implementation. According to one or more embodiments, the trapping masses are used in at least two reactors, preferably arranged in series. According to one or more embodiments, the feed lines of the reactors are equipped with a bypass line. The process according to the invention can advantageously be carried out without the trapping of the silicon species being interrupted during a change of mass made necessary after a certain period of use. Specifically, when a mass for trapping the silicon species is saturated, the reactor in which it is used is disconnected from the feedstock to be purified containing silicon species via, for example, a bypass line. At the same time, the feedstock to be purified can then continue to be treated by passing through the other (or several other) reactor(s) containing masses for trapping silicon species that have trapping capacities for silicon species.

According to one or more embodiments, the trapping masses are used in several reactors and the operating conditions for the various trapping steps in the various reactors are identical or different. According to one or more embodiments, the operating conditions for trapping Si (defined by T1, $P_1$, LHSV1 or GHSV) in a first reactor and the operating conditions (defined by T2, $P_2$, LHSV2 or GHSV2) in a second reactor (placed for example downstream of the first reactor with respect to the direction of flow of the feedstock to be treated) are such that at least one of the operating conditions of temperature, pressure, LHSV and GHSV satisfies:

$T1 \leq T2$;

$P1 \leq P2$;

LHSV1≤LHSV2 or GHSV1≤GHSV2.

The contact of the feedstock with the trapping mass advantageously makes it possible to trap the silicon species contained in the feedstock to be treated and to obtain an effluent having a reduced content of silicon species compared with the content of the initial feedstock, or even to completely remove the silicon species from the feedstock.

According to one or more embodiments, the contact of the feedstock with the trapping mass makes it possible to simultaneously remove, at least in part, the silicon species and certain other impurities, such as, for example, sulfur compounds and/or nitrogen compounds.

Prior to the implementation of the process according to the invention, the gaseous or liquid feed can be pretreated. Said pretreatment can consist of a heating or a cooling, of a compression or of an expansion (in the case of a gaseous feedstock), and/or of a purification treatment for removing or reducing the content, in the feedstock, of one or more compounds considered undesirable.

According to one or more embodiments, when the composition of the feedstock requires it, the feedstock can be subjected, prior to its use in the process according to the invention, to a step of selective hydrogenation of the unsaturated hydrocarbon compounds and coke precursors, such as diolefins. This pretreatment aims to reduce or eliminate the formation of coke during the implementation of the process according to the invention, on the surface of the silicon-trapping mass which can degrade the capacity of the mass by limiting access to the silicon-trapping sites by covering said sites. This pretreatment requires a supply of hydrogen in a small amount, linked to the concentration of unsaturated coke precursor compounds in the feedstock. According to one or more embodiments, the amount of hydrogen can be calculated from the composition of the feedstock so that the hydrogen is substantially entirely consumed during this selective hydrogenation step and so that at the end of this step, the hydrogen concentration is negligible or in trace amounts. According to one or more embodiments, the amount of hydrogen present at the inlet of the hydrogenation step is substantially stoichiometric with respect to the value needed to hydrogenate the diolefins. According to one or more embodiments, the selective hydrogenation step is carried out at a temperature of between 20° C. and 300° C., preferably 50° C. and 250° C., very preferably between 80° C. and 200° C., a pressure of between 0.4 MPa and 5 MPa, preferably between 1 MPa and 3 MPa, and a liquid hourly space velocity of between 1 $h^{-1}$ and 10 $h^{-1}$ or a gas hourly space velocity of between 100 and 1000 $h^{-1}$, with, in the case of a liquid feedstock, a volume ratio between the dihydrogen and the liquid feedstock to be treated of between 1 and 500 $Nm^3/m^3$ and, in the case of a gaseous feedstock, a $PpH_2$ of between 0.01 MPa (0.1 bar) and 5 MPa (50 bar). According to one or more embodiments, the selective hydrogenation step is carried out using a catalyst, for example a palladium catalyst, such as a catalyst comprising a support based on alumina or consisting of alumina and comprising palladium, such as between 0.1% and 1% by weight of palladium relative to the total weight of the catalyst. In the case of a gasoline, the selective hydrogenation pretreatment is generally carried out under mild conditions (T<250° C.) and aims to hydrogenate the diolefins without affecting the olefins, in order to preserve the engine characteristics of the gasoline (engine octane numbers).

According to one or more embodiments, the selective hydrogenation pretreatment step and the silicon trapping purification step are carried out in the same chamber (in the same reactor), by positioning the selective hydrogenation catalyst at the reactor inlet and then the trapping mass in a second (downstream) zone of the reactor.

The effluent resulting from the process according to the invention can advantageously be hydrotreated. The effluent resulting (directly) from the process according to the invention can advantageously undergo at least one hydrodesulfurization and/or hydrodenitrogenation step.

According to one or more embodiments, the purified effluent resulting from the silicon trapping step, the silicon content of which is reduced relative to the initial content in the feedstock, is sent to at least one other purification step in order to eliminate or reduce the content of other undesirable elements, including sulfur or nitrogen in particular, with a view to improving the quality of the product. This involves for example one or more desulfurization or hydrotreating steps. Mention may be made, for example, of the desulfurization of the gasolines required to meet the gasoline specifications (e.g. sulfur content of less than 10 ppm by weight). These additional post-treatments generally require the presence of hydrogen. This new purification step can be carried out in one or more reactors, which can be operated in the presence of one or more catalysts. Generally, these catalytic solids are composed of one or more metals M (M1M2Mi) on support(s), Mi belonging in particular to groups VIB or VIII. In the case where several catalytic solids are used in this other purification step, they can be loaded as a multilayer in the same reactor or in different reactors. They can be operated under different conditions, and this is often the case.

The trapping mass according to the invention is any type of trapping mass or combination of trapping masses, known to those skilled in the art as being effective for removing silicon species, for example one or more trapping masses based on a porous refractory oxide and in particular based on alumina or silica-alumina. According to one or more embodiments, the trapping mass comprises a porous support based essentially on alumina, and optionally at least one metal from the metals from groups VIB and VIII. The group VIB metal(s) are preferentially chosen from molybdenum and tungsten. The group VIII metal(s) are preferentially chosen from iron, cobalt and nickel. According to one or more embodiments, the trapping mass comprises a metal from the group VIB metals and a metal from the group VIII metals. According to one or more embodiments, the trapping mass comprises nickel and molybdenum.

According to one or more embodiments, the content of group VIB metal, expressed as oxide, is less than 20% by weight, relative to the total weight of the trapping mass. According to one or more embodiments, the content of group VIB metal, expressed as oxide, is between 0.1% and 20% by weight, preferably between 1% and 15% by weight and more preferably between 2% and 10% by weight, relative to the total weight of the trapping mass. According to one or more embodiments, the content of group VIB metal, expressed as oxide, is less than 7% by weight, preferably less than 6% by weight, relative to the total weight of the trapping mass.

According to one or more embodiments, the content of group VIII metal, expressed as oxide, is less than 10% by weight, relative to the total weight of the trapping mass. According to one or more embodiments, the content of group VIII metal, expressed as oxide, is between 0.01% and 10% by weight, preferably between 0.1% and 7% by weight and more preferably between 0.2% and 5% by weight, relative to the total weight of the trapping mass. According to one or more embodiments, the content of group VIII metal, expressed as oxide, is less than 3% by weight, preferably less than 2% by weight, preferably less than or equal to 1% by weight, relative to the total weight of the trapping mass.

According to one or more embodiments, the trapping mass advantageously comprises at least one phosphorus compound. According to one or more embodiments, the content of phosphorus, expressed as oxide $P_2O_5$, is less than 15% by weight, relative to the total weight of the trapping mass. According to one or more embodiments, the content of P, expressed as oxide $P_2O_5$, is between 0.01% and 15% by weight, preferably between 0.05% and 10% by weight and more preferably between 0.1% and 9% by weight, for instance between 0.15% and 8% by weight or else between 0.2% and 7% by weight, relative to the total weight of the trapping mass. According to one or more embodiments, the content of P, expressed as oxide $P_2O_5$, is between 0.25% and 5% by weight, preferably between 0.3% and 4% by weight and more preferably between 0.5% and 3% by weight.

According to the invention, the trapping mass has a specific surface area of at least 200 $m^2/g$, preferably of at least 290 or 300 $m^2/g$. According to one or more embodiments, the trapping mass has a specific surface area of between 300 and 400 $m^2/g$, preferably between 310 and 370 $m^2/g$, preferably between 320 and 360 $m^2/g$, preferably between 320 and 350 $m^2/g$.

According to one or more embodiments, the trapping mass has a grain density of at least 0.2 g/ml and preferably of at least 0.4 g/ml. According to one or more embodiments, the trapping mass has a grain density of between 0.2 and 2 g/ml, preferably between 0.4 and 1.5 g/ml.

According to one or more embodiments, the trapping mass has a grain density of between 0.5 and 1.4 g/ml, preferably between 0.6 and 1.3 g/ml, for instance between 0.7 and 1.2 g/ml.

According to one or more embodiments, the pores of the trapping mass have a mean size (or mean diameter) of less than 50 nm, preferably of less than or equal to 30 nm. According to one or more embodiments, the pores of the trapping mass have a mean size of between 1 nm and 30 nm, preferably between 5 nm and 10 nm, preferably between 5 nm and 9 nm.

According to one or more embodiments, the trapping mass has a monomodal pore size distribution. According to one or more embodiments, the pores of the trapping mass having a mean size of less than 10 nm have a monomodal pore size distribution.

According to one or more embodiments, the trapping mass has a total pore volume (TPV) of between 0.15 $cm^3/g$ and 1.5 $cm^3/g$, preferably between 0.2 $cm^3/g$ and 1.0 $cm^3/g$. According to one or more embodiments, the trapping mass has a total pore volume (TPV) of between 0.25 $cm^3/g$ and 0.9 $cm^3/g$, preferably between 0.3 $cm^3/g$ and 0.8 $cm^3/g$. According to one or more embodiments, at least 80%, preferably at least 85% and even more preferably at least 90% of the total pore volume corresponds to the volume of the pores with a diameter of less than 50 nm, preferably with a diameter of less than 10 nm.

Surprisingly, such a selection of size of pores makes it possible to increase the trapping capacity of the trapping mass in silicon compounds and in particular for organosilicon compounds. Without being committed to a particular theory, it appears that such small pores might make it possible to better retain the species by a confinement effect which would be additional to the conventional mechanism.

According to one or more embodiments, the porous support of the trapping mass is based on alumina. According to one or more embodiments, the porous support is essentially alumina. According to one or more embodiments, the porous support is based on transition alumina. According to one or more embodiments, the porous support consists essentially of transition alumina.

According to one or more embodiments, the alumina(s) of the porous support of the trapping mass are of $\chi$, $\eta$, $\gamma$ or $\delta$ type. Preferably, they are of $\gamma$ or $\delta$ type. More preferably still, they are of $\gamma$ type.

According to one or more embodiments, the porous support consists essentially of a plurality of juxtaposed agglomerates.

According to one or more embodiments, the trapping mass is provided in the form of extrudates of cylindrical, hollow cylinder, cartwheel, trilobe or multilobe shape or any other geometric shape used by a person skilled in the art. According to one or more embodiments, the trapping mass exhibits a diameter of between 0.5 and 10 mm, preferably between 0.8 and 3.2 mm, and/or a length of between 1 mm and 20 mm, preferably between 1 and 10 mm, in particular when the trapping mass is employed in a fixed bed.

According to one or more embodiments, the trapping mass is provided in the bead form. According to one or more embodiments, the trapping mass exhibits a diameter of between 0.5 and 10 mm, preferably between 0.8 at 3.2 mm.

The process according to the present invention makes it possible to purify both liquid and gaseous hydrocarbon feedstocks.

The gaseous or liquid hydrocarbon feedstock to be treated can contain silicon compounds, in various forms. For example, silicon can be found in inorganic form, that is to say silica, and in organic form. In organic form, the silicon can be contained in polymers, for example polydimethylsiloxane, or in smaller molecules, such as siloxanes, which are linear or cyclic, silanes, ethoxysilanes, silanols or silanediols, and the like. The concentration of silicon compounds in the gaseous or liquid effluent to be treated can be variable. The gaseous feedstock to be treated can contain between 10 ng and 1 g of silicon per $Nm^3$ of gas. The liquid feedstock to be treated can contain for example between 10 ng and 100 g of silicon per $m^3$ of liquid. Since silicon in its various forms, in particular organic form, is detrimental for reasons of efficacy of the downstream treatments of the feedstock, the siliceous compounds are advantageously separated owing to the implementation of the process according to the invention. The feedstock to be treated can also contain other elements, such as sulfur, nitrogen or chlorine, in various forms. In particular, the sulfur can be present in the form of organosulfur compounds, for example in the form of mercaptans, sulfides, disulfides or thiophene compounds. The sulfur content of the effluent may be between 0% by weight or 0.1% by weight and 10% by weight, the nitrogen content may be between 0% by weight or 0.1% by weight and 10% by weight and the chlorine content may be between 0% by weight or 0.1% by weight and 1% by weight. Advantageously, neither the nitrogen nor the sulfur nor the chlorine which may be present in the feedstock to be treated causes losses of performance in the process according to the invention.

The use of the process according to the invention is particularly suitable for the treatment of liquid or gaseous feedstocks of petroleum origin and the derivatives thereof, notably for the treatment of liquid or gaseous feedstocks from conversion units and advantageously from thermal conversion units. The use of the process according to the invention is particularly suitable for the treatment of liquid or gaseous feedstocks resulting from the degradation of biomass, waste or of manufactured products, such as plastics. It is common for such feedstocks to contain silicon compounds. The gaseous or liquid feedstock to be treated in the process according to the invention can advantageously be chosen from the group consisting of combustion flue gases, synthesis gas, natural gas, natural gas condensates, oil or crude oils, liquid or gaseous petroleum cuts, liquid hydrocarbon cuts from refineries or petrochemical plants, effluents resulting from Fischer-Tropsch synthesis processes (e.g. XTL, such as Gas-To-Liquid and/or Biomass-To-Liquid), petrochemical intermediates, oils resulting from the pyrolysis of biomass or plastics, biogas, coker or catalytic cracking (or FCC for Fluid Catalytic Cracking) gasolines, and their mixtures. According to one or more embodiments, the feedstock is a natural-gas condensate. According to one or more embodiments, the feedstock is a coker or FCC gasoline, such as a C5-250° C. gasoline cut resulting from an FCC catalytic cracking refining process or resulting from a coking unit.

According to one or more embodiments, the combustion flue gases are produced in particular by the combustion of hydrocarbons, of biogas and of coal in a boiler or by a combustion gas turbine, for example with the aim of producing electricity. These flue gases can comprise, by volume, between 50% and 80% of nitrogen, between 5% and 40% of carbon dioxide, between 1% and 20% of oxygen, and potentially impurities, such as SOX and NON.

According to one or more embodiments, the synthesis gas is a gas containing carbon monoxide CO, molecular hydrogen $H_2$ (e.g., in an $H_2/CO$ molar ratio generally equal to approximately 2±1), water vapor (e.g., generally at saturation), methane and carbon dioxide $CO_2$ (for example, at a content generally of approximately 10%±5% by volume). The synthesis gas can additionally contain sulfur-comprising impurities ($H_2S$, COS, and the like), nitrogen-comprising impurities ($NH_3$, HCN, and the like) and halogen-comprising impurities.

According to one or more embodiments, the natural gas consists predominantly of gaseous hydrocarbons but can contain several of the following acidic compounds: carbon dioxide $CO_2$, hydrogen sulfide $H_2S$, mercaptans, carbon oxysulfide COS and carbon disulfide $CS_2$. The content of the natural gas in these acidic compounds is highly variable and can range from 0% to 40% by volume for the $CO_2$ and the $H_2S$.

According to one or more embodiments, the natural gas condensates consist of liquid hydrocarbons, the production of which is associated with the production of natural gas. These complex liquid mixtures are very similar to light crude oils.

Mention may in particular be made, among the liquid hydrocarbons from refineries, of LPGs (C3-C4 cut), naphthas (C5-C8 cut), kerosenes and diesel oils. Mention may in particular be made, among the liquid hydrocarbons from petrochemical plants, of LPGs (C3-C4 cut) and gasolines from cracking and steam cracking (or Pyrolysis Gasoline, also called PyGas).

Mention may in particular be made, among the oils resulting from the pyrolysis of biomass or of plastics, of the oils, advantageously in liquid form at ambient temperature, resulting from the pyrolysis of plastics, preferably of plastic waste originating in particular from collection and sorting channels. According to one or more embodiments, the oils resulting from the pyrolysis of biomass or of plastics comprise a mixture of hydrocarbon compounds, in particular paraffins, monoolefins and/or diolefins, naphthenes and aromatics, said hydrocarbon compounds preferably having a boiling point of less than 700° C. and preferably of less than 550° C. The plastics pyrolysis oil can comprise impurities, such as metals, in particular silicon and iron, or halogenated compounds, in particular chlorinated compounds.

According to one or more embodiments, biogas is a gas produced by the methanization or also the fermentation of animal or vegetable organic matter in the absence of oxygen. It can be produced naturally, such as, for example, in landfills containing organic waste, or artificially in methanizers or digesters supplied with animal manure, organic or agricultural waste, or sludges from water treatment plants. Biogas consists predominantly (e.g., at least 50% by volume) of methane and $CO_2$, the proportion of which varies according to the origin of the starting material used.

EXAMPLES

Example 1

A trapping mass M1 is prepared by depositing NiO, $MoO_3$ and $P_2O_5$ on an alumina support.

The trapping mass M1 was prepared in the following manner:
a) a porous alumina support is provided;
b) an impregnation solution is prepared. 60% of the total volume of water of the impregnation solution is poured into a round-bottomed flask. The desired amount of phosphoric acid is subsequently added. The molybdenum and nickel precursors are successively added to the solution while stirring the mixture. This solution is left stirring and at reflux at 90° C. When the solution has become clear, reflux is halted. When the solution is at ambient temperature, water is added in order to obtain 95% of the targeted total volume of the impregnation solution.
c) the porous support is impregnated by slow spraying with said solution prepared in the preceding step b).
d) the product obtained in the preceding step c) is left maturing in a closed vessel for 3 hours at room temperature.
e) the material obtained in the preceding step d) is dried at 90° C. for 3 h;
f) the material obtained in the preceding stage e) is calcined in a tube furnace at 450° C. under a humid atmosphere for 45 min.

The nickel, molybdenum and phosphorus contents of the trapping masses were measured by X-ray fluorescence on an Axios mAX device from PANanalytical. The contents are respectively 1.13, 5.24 and 2.05 expressed as weight percentages of the corresponding oxides relative to the total weight of the trapping mass.

The pore volume, the average pore diameter, the specific surface area and the tapped packing density (TPD) of the support are respectively 0.5 ml/g, 7.6 nm, 321 m²/g and 0.67 g/ml. The 5 grain density and mean diameter of the pores were determined from the mercury porosimetry results and specific surface area from the $N_2$ adsorption isotherm at 77K (cf. Rouquerol F., Rouquerol J. and Sing K., "Adsorption by Powders and Porous Solids: Principle, Methodology and Applications", Academic Press, 1999).

The trapping mass M1 is tested for the trapping of silicon compounds in a pilot unit equipped with a fixed-bed reactor, regulated in terms of pressure and temperature. The unit is fed by an FCC gasoline feedstock (50°–250° C. cut from a catalytic cracking refining unit) doped with 50 ppm of silicon in D3 or D4 form (D3/D4 ratio: 50/50), D3 (hexamethylcyclotrisiloxane) and D4 (octamethylcyclotetrasiloxane) being two cyclic dimethylsiloxanes (trimer or tetramer), main decomposition compounds of the PDMS (polydimethylsiloxane) defoamer polymer. This feedstock is sent through the fixed bed of mass M1, of volume 40 cm³ at 300° C. under 2 MPa (20 bar) in the presence of $H_2$ with an $H_2$/feedstock ratio of 150 Nm³/m³ at LHSV values of 1, 2 and 4 h$^{-1}$ in 3 cases according to the invention and at LHSV values of 5 and 8 h$^{-1}$ in two other (comparative) cases. Samples are withdrawn twice daily and analyzed by X-ray fluorescence in order to determine their silicon content. The test is halted when the silicon concentration at the outlet in the effluent is equivalent to 60% of the concentration at the inlet of the feedstock and a material balance with regard to the silicon is carried out: the difference between what entered the column and what exited therefrom corresponds to the weight of silicon trapped on the trapping masses. Table 1 presents the silicon content in % by weight expressed as Si trapped by the trapping mass.

TABLE 1

| LHSV (h$^{-1}$) | % Si |
| --- | --- |
| 1 (according to the invention) | 9.1 |
| 2 (according to the invention) | 7.4 |
| 4 (according to the invention) | 5.3 |
| 5 (comparative) | 4.7 |
| 8 (comparative) | 4.4 |

The results shown in table 1 above clearly show a significant gain in silicon trapping performance by reducing the LHSV when operating at an LHSV below 5 h$^{-1}$. The capacity attained increases by 22% on going from operation at an LHSV of 2 h$^{-1}$ to 1 h$^{-1}$, i.e. 22% per unit of LHSV (7.4 g of silicon trapped per 100 g of mass in the operation at LHSV of 2 h$^{-1}$ compared to 9.1 g/100 g for LHSV of 1 h$^{-1}$) and by 40% on going from operation at an LHSV of 4 h$^{-1}$ to 2 h$^{-1}$, i.e. 20% per unit of LHSV (5.3 g of silicon trapped per 100 g of mass in the operation at LHSV of 4 h$^{-1}$ compared to 7.4 g/100 g for LHSV of 2 h$^{-1}$). In contrast, in the LHSV range of at least 5 h$^{-1}$ the effect of reducing the LHSV is much less noticeable: going from an LHSV of 8 h$^{-1}$ to 5 h$^{-1}$ only makes it 5 possible to gain 7% capacity, i.e. 2.3% per unit of LHSV (4.4 g of silicon trapped per 100 g of mass in the operation at LHSV for 8 h$^{-1}$ compared to 4.7 g/100 g for an LHSV of 5 h$^{-1}$).

The invention claimed is:

1. A process for trapping Silicon compounds in a gaseous or liquid feedstock, comprising bringing the feedstock into contact with a trapping mass with a liquid hourly space velocity LHSV of less than 5 h$^{-1}$ or a gas hourly space velocity GHSV of less than 500 h$^{-1}$, said trapping mass comprising a metal from the group VIB metals in a content, expressed as oxide, being less than 6% by weight, relative to the total weight of the trapping mass and a metal from the group VIII metals.

2. The trapping process as claimed in claim 1, wherein the liquid hourly space velocity LHSV is less than 4.5 h$^{-1}$, or the gas hourly space velocity GHSV is less than 450 h$^{-1}$.

3. The trapping process as claimed in claim 1, wherein the contact is carried out at a temperature of between 20° C. and 500° C. and a pressure of between 0.1 and 10 MPa.

4. The trapping process as claimed in claim 1, wherein the contact is carried out in the presence of dihydrogen, wherein the feedstock is liquid and the ratio of the gaseous volume flow rate of dihydrogen to the liquid volume flow rate of liquid feedstock is between 0 and 1000 Nm$^3$/m$^3$, or wherein the feedstock is gaseous and the dihydrogen partial pressure PpH$_2$ is between 0.01 MPa and 10 MPa.

5. The trapping process as claimed in claim 1, wherein the trapping mass is arranged in a fixed bed.

6. The trapping process as claimed in claim 1, wherein the trapping mass comprises a plurality of trapping masses positioned as a mixture or multilayer.

7. The trapping process as claimed in claim 1, wherein the trapping mass comprises trapping masses arranged in a trapping unit comprising at least two reactors, positioned in series or in parallel.

8. The trapping process as claimed in claim 7, wherein the operating conditions of each of the reactors are identical or different.

9. The trapping process as claimed claim 1, further comprising a pretreatment step upstream of the contacting step, wherein unsaturated organic compounds are reduced or eliminated.

10. The trapping process as claimed in claim 9, wherein the pretreatment step is a selective hydrogenation step.

11. The trapping process as claimed in claim 1, wherein an effluent depleted in silicon compounds is sent to a hydrotreating section.

12. The trapping process as claimed in claim 1, wherein the trapping mass is positioned at an inlet of a hydrotreating reactor.

13. The trapping process as claimed in claim 1, wherein the trapping mass contains alumina.

14. The trapping process as claimed in claim 1, wherein the trapping mass has at least one of the following characteristics: γ-type support, presence of group VIB metal with a content of less than 20% by weight of group VIB metal expressed as oxide, presence of group VIII metal with a content of less than 10% by weight of group VIII metal expressed as oxide, presence of phosphorus with a content of less than 15% by weight of P expressed as oxide P$_2$O$_5$, grain density at least 0.2 g/ml, specific surface area at least 200 m$^2$/g, average pore size of less than 50 nm, and/or total pore volume of between 0.15 cm$^3$/g and 1.5 cm$^3$/g.

15. The trapping process as claimed in claim 1, wherein the feedstock is selected from the group consisting of combustion flue gases, synthesis gas, natural gas, natural-gas condensates, petroleum, petroleum crudes, liquid petroleum cuts, gaseous petroleum cuts, liquid hydrocarbon cuts from refineries, liquid hydrocarbon cuts from petrochemical plants, effluents resulting from Fischer-Tropsch synthesis processes, petroleum petrochemical intermediates, oils resulting from the pyrolysis of biomass, oils resulting from the pyrolysis of biomass plastics, biogas, coking gasoline, catalytic cracking gasoline, and mixtures thereof.

16. The trapping process as claimed in claim 1, wherein the trapping mass has all of the following characteristics: γ-type support, presence of group VIB metal with a content of less than 20% by weight of group VIB metal expressed as oxide, presence of group VIII metal with a content of less than 10% by weight of group VIII metal expressed as oxide, presence of phosphorus with a content of less than 15% by weight of P expressed as oxide P$_2$O$_5$, grain density at least 0.2 g/ml, specific surface area at least 200 m$^2$/g, average pore size of less than 50 nm, and total pore volume of between 0.15 cm$^3$/g and 1.5 cm$^3$/g.

17. The trapping process as claimed in claim 1, wherein the contact is carried out in the presence of dihydrogen, wherein the feedstock is liquid and the ratio of the gaseous volume flow rate of dihydrogen to the liquid volume flow rate of liquid feedstock is between 0.1 and 1000 Nm$^3$/m$^3$, or wherein the feedstock is gaseous and the dihydrogen partial pressure PpH$_2$ is between 0.01 MPa and 9 MPa.

18. The trapping process as claimed in claim 1, wherein the feedstock is liquid.

19. The trapping process as claimed in claim 1, wherein the feedstock is gaseous.

20. The trapping process as claimed in claim 1, wherein the liquid hourly space velocity LHSV is 0.25 to 4 h$^{-1}$, or the gas hourly space velocity GHSV is 25 to 400 h$^{-1}$.

* * * * *